United States Patent
West, Jr.

(10) Patent No.: US 8,394,088 B2
(45) Date of Patent: *Mar. 12, 2013

(54) ELECTROSURGICAL INSTRUMENT WITH AN ABLATION MODE AND A COAGULATION MODE

(75) Inventor: Hugh S. West, Jr., Sandy, UT (US)

(73) Assignee: HS West Investments, LLC, Sandy, UT (US)

( * ) Notice: Subject to any disclaimer, the term of this patent is extended or adjusted under 35 U.S.C. 154(b) by 281 days.

This patent is subject to a terminal disclaimer.

(21) Appl. No.: 12/651,892

(22) Filed: Jan. 4, 2010

(65) Prior Publication Data
US 2010/0106153 A1    Apr. 29, 2010

Related U.S. Application Data

(63) Continuation-in-part of application No. 12/171,150, filed on Jul. 10, 2008.

(51) Int. Cl.
*A61B 18/14*    (2006.01)
(52) U.S. Cl. ............................................. 606/37; 606/41
(58) Field of Classification Search .................... 606/37, 606/39, 40, 42; 607/148; 600/393
See application file for complete search history.

(56) References Cited

U.S. PATENT DOCUMENTS

| | | |
|---|---|---|
| 4,532,924 A | 8/1985 | Auth et al. |
| 4,998,933 A | 3/1991 | Eggers et al. |
| 5,178,620 A | 1/1993 | Eggers et al. |
| 5,364,395 A | 11/1994 | West, Jr. |
| 5,366,443 A | 11/1994 | Eggers et al. |
| 5,419,767 A | 5/1995 | Eggers et al. |
| 5,662,680 A | 9/1997 | Desai |
| 5,860,920 A | 1/1999 | McGee et al. |
| 5,904,681 A | 5/1999 | West, Jr. |
| 5,938,661 A * | 8/1999 | Hahnen .......................... 606/46 |
| 6,024,733 A | 2/2000 | Eggers et al. |
| 6,064,905 A | 5/2000 | Webster, Jr. et al. |
| 6,113,595 A | 9/2000 | Muntermann |
| 6,117,131 A | 9/2000 | Taylor |
| 6,168,593 B1 | 1/2001 | Sharkey et al. |
| 6,238,391 B1 | 5/2001 | Olsen et al. |
| 6,241,724 B1 | 6/2001 | Fleischman et al. |
| 6,254,600 B1 | 7/2001 | Willink et al. |
| 6,264,650 B1 | 7/2001 | Hovda et al. |
| 6,379,350 B1 | 4/2002 | Sharkey et al. |
| 6,494,881 B1 * | 12/2002 | Bales et al. ..................... 606/45 |
| 6,546,270 B1 | 4/2003 | Goldin et al. |

(Continued)

FOREIGN PATENT DOCUMENTS

JP    2007044281    2/2007

OTHER PUBLICATIONS

ConMed Linvatec—Anthroscopy—Electrodes, Apr. 15, 2008 http://www.conmed.com/products_smjoint_electrodes.php.

(Continued)

*Primary Examiner* — Michael Peffley
*Assistant Examiner* — Thomas Giuliani
(74) *Attorney, Agent, or Firm* — Workman Nydegger

(57) ABSTRACT

Electrosurgical instruments are configured to selectively perform ablation or coagulation as desired. The electrosurgical instruments include at least two electrodes on the electrode probe that can be activated using an RF generator. The electrosurgical instruments are selectively switchable between an ablation mode and a coagulation mode by changing the amount of active electrode surface area. In particular, in the ablation mode, a relatively small electrode surface area is active. Thus, for a given power input, the current density is relatively high. In the coagulation mode, the active electrode surface area is increased, thereby reducing the current density in the coagulation mode for the given power input.

30 Claims, 9 Drawing Sheets

U.S. PATENT DOCUMENTS

| | | | |
|---|---|---|---|
| 6,565,561 B1 | 5/2003 | Goble et al. | |
| 6,592,580 B1 | 7/2003 | Stockert | |
| 6,632,193 B1 | 10/2003 | Davison et al. | |
| 6,813,520 B2 | 11/2004 | Sampson et al. | |
| 6,991,631 B2 | 1/2006 | Woloszko et al. | |
| 7,150,746 B2 | 12/2006 | DeCesare et al. | |
| 7,244,256 B2 | 7/2007 | DeCesare et al. | |
| 7,537,595 B2* | 5/2009 | McClurken | 606/50 |
| 7,563,261 B2 | 7/2009 | Carmel et al. | |
| 2002/0049438 A1* | 4/2002 | Sharkey et al. | 606/41 |
| 2005/0124915 A1 | 6/2005 | Eggers et al. | |
| 2005/0283151 A1* | 12/2005 | Ebbutt et al. | 606/50 |
| 2006/0129145 A1* | 6/2006 | Woloszko et al. | 606/41 |
| 2007/0179495 A1* | 8/2007 | Mitchell et al. | 606/41 |
| 2008/0077128 A1* | 3/2008 | Woloszko et al. | 606/41 |
| 2008/0140074 A1* | 6/2008 | Horne et al. | 606/42 |
| 2008/0167645 A1* | 7/2008 | Woloszko | 606/40 |
| 2008/0234673 A1* | 9/2008 | Marion et al. | 606/45 |
| 2010/0010485 A1* | 1/2010 | West, Jr. | 606/37 |

OTHER PUBLICATIONS

MedWaves, Inc. Announces Receipt of United States Food and Drug Administration 510K, Apr. 15, 2008 http://www.reuters.com/article/pressRelease/idUS238383+31-Jan-2008+PRN20080131.

U.S. Appl. No. 12/171,150, filed Jul. 10, 2008, Office Action dated Jun. 22, 2011.

\* cited by examiner

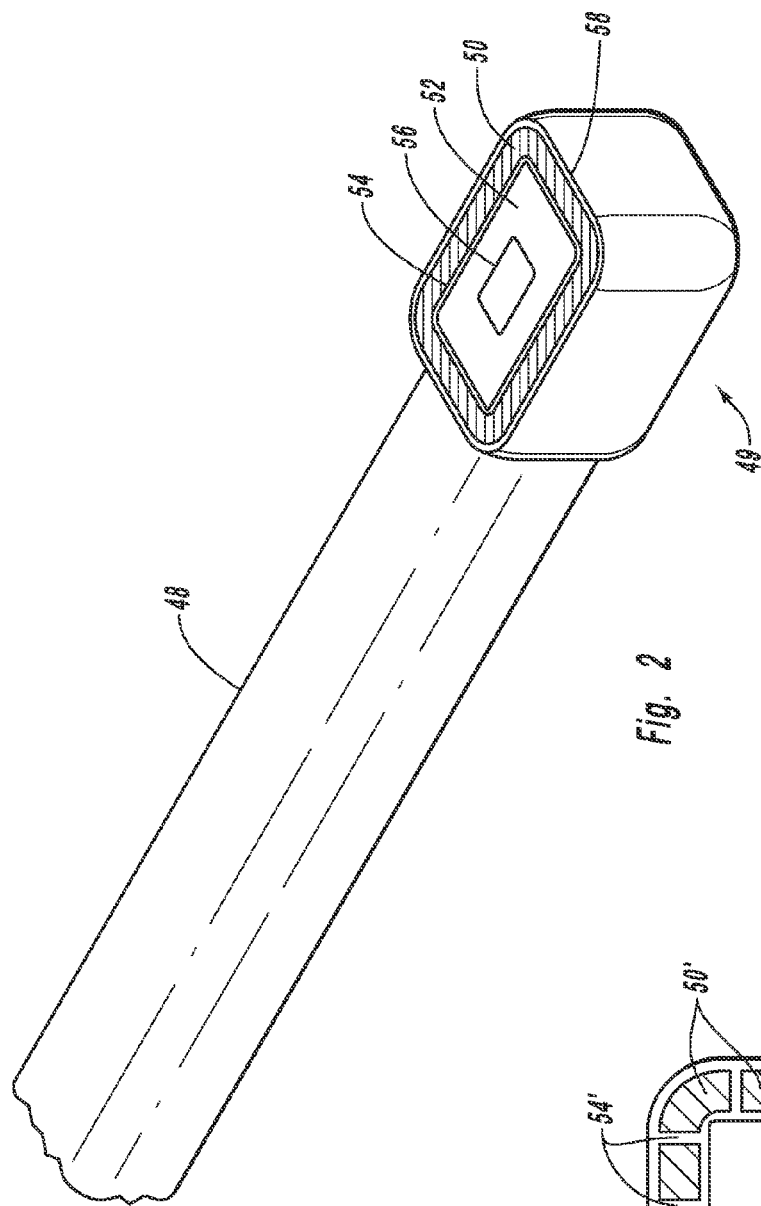
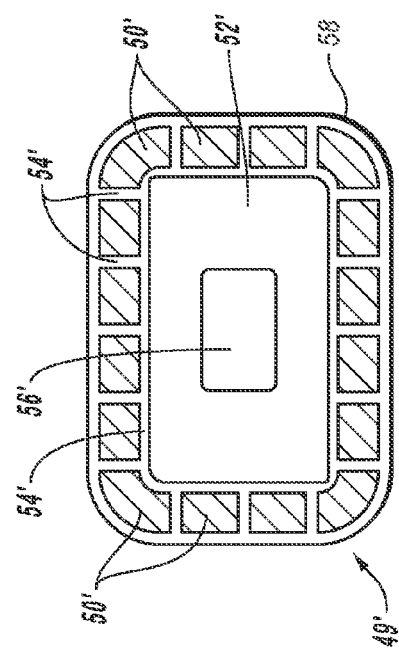

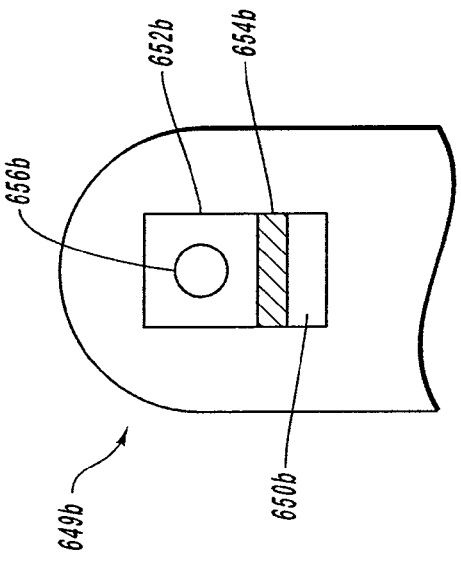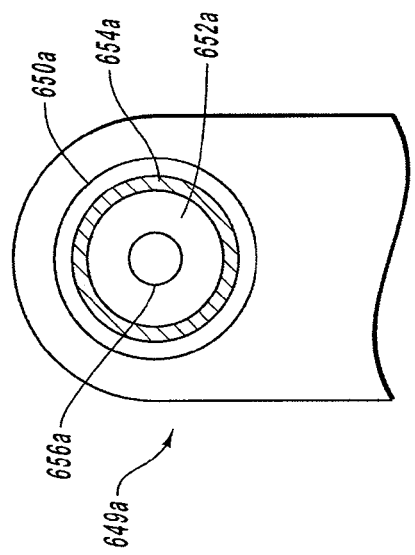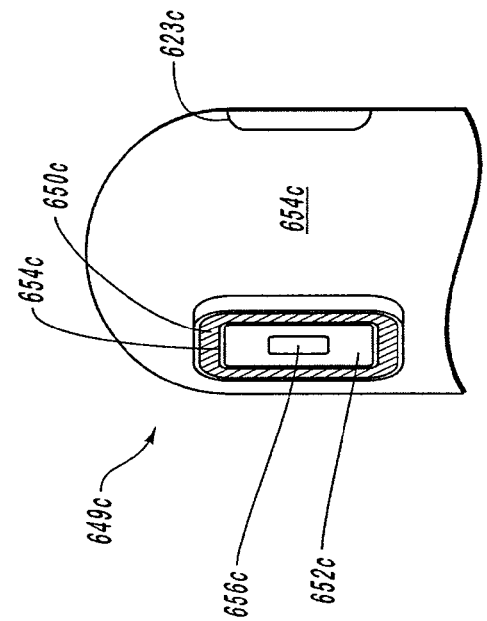
Fig. 6A
Fig. 6B
Fig. 6C

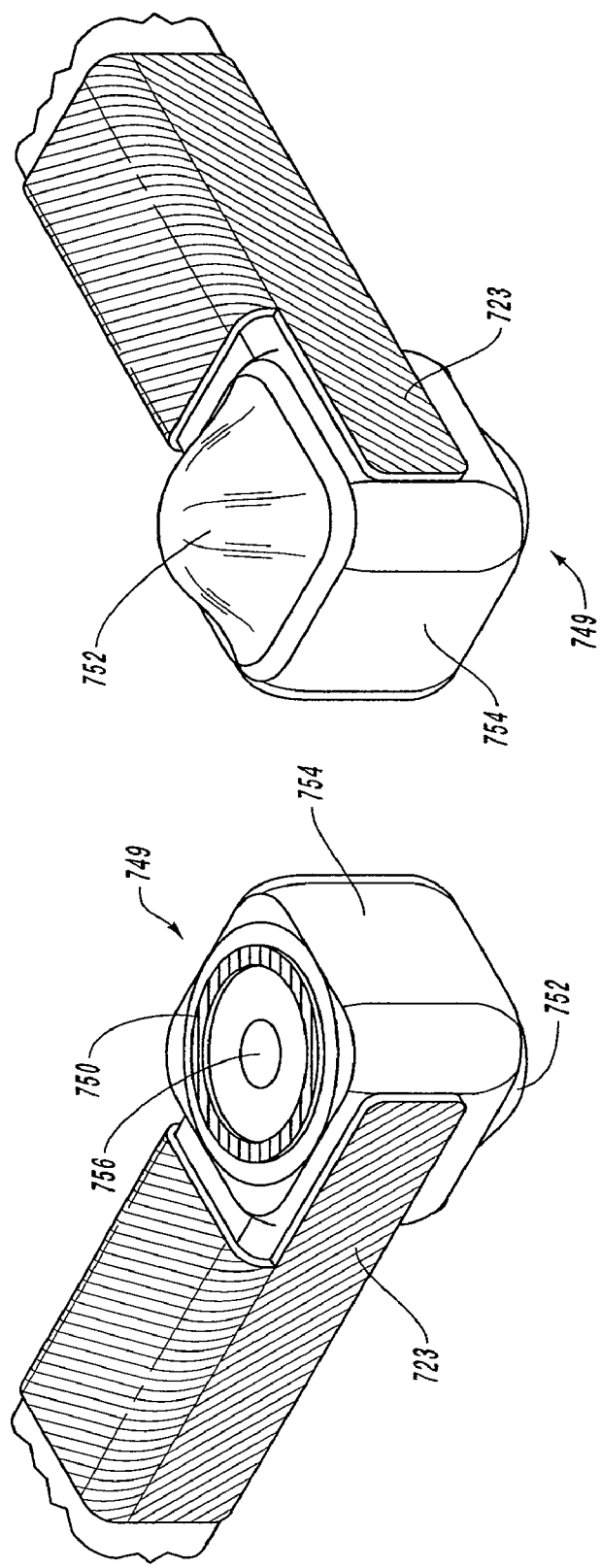

US 8,394,088 B2

ELECTROSURGICAL INSTRUMENT WITH AN ABLATION MODE AND A COAGULATION MODE

CROSS-REFERENCE TO RELATED APPLICATION

This application is a continuation-in-part of co-pending U.S. patent application Ser. No. 12/171,150, filed Jul. 10, 2008, the disclosure of which is incorporated herein in its entirety.

BACKGROUND OF THE INVENTION

1. The Field of the Invention

The present invention relates to electrosurgical instruments for alternatively ablating and coagulating tissue in an arthroscopic procedure.

2. The Relevant Technology

Electrosurgical procedures utilize an electrosurgical generator to supply radio frequency (RF) electrical power to an active electrode for cutting and/or coagulating tissue. An electrosurgical probe is generally composed of a metallic conductor surrounded by a dielectric insulator such as plastic, ceramic, or glass. The surface of the electrode remains exposed and provides the cutting or ablating surface. During an electrosurgical procedure, the metal electrode is often immersed in a conducting fluid and is brought in contact with or in close proximity to the tissue structure to be ablated or coagulated. During a procedure, the probe is typically energized at a voltage of a few hundred to a few thousand volts and at a frequency between 100 kHz to over 4 MHz. The voltage induces a current in the conductive liquid, which causes heating. The most intense heating occurring in the region very close to the electrode where the current density is highest.

Depending on how the electrosurgical instrument is configured, the heat generated from the device can be used to coagulate tissue (e.g., cauterize tissue) or alternatively to ablate tissue (i.e., cut tissue). To cause ablation (i.e., cutting), the electrode generates enough heat to form gas bubbles around the electrode. The gas bubbles have a much higher resistance than tissue or saline, which causes the voltage across the electrode to increase. Given sufficient power, the electrode discharges (i.e., arcs). The high voltage current travels through the gas bubbles and creates a plasma discharge. Moving the electrode close to tissue causes the plasma layer to come within a distance sufficiently close to remove or ablate the tissue.

Electrosurgical instruments can also be used for coagulating tissue. In coagulation, the current density at the electrode is configured to cause heating without cutting. The current density is kept sufficiently high to cause proteins and/or other components of the tissue to agglomerate, thereby causing coagulation. However, during coagulation, the electrode's current density is limited to prevent ablation.

Some existing electrosurgical instruments can perform both ablation and coagulation. In most cases, the physician switches between the ablation mode and the coagulation mode by reducing the power from the RF generator. Reducing the power output of the RF generator reduces the current density at the electrode, which prevents the electrode from arcing and generating a plasma. Consequently, the electrosurgical instrument will cause coagulation. Once the physician has completed the desired coagulation, the power of the RF generator can be increased to return to the ablation mode.

BRIEF SUMMARY OF THE INVENTION

The present invention is directed to an electrosurgical instrument that can selectively perform ablation or coagulation. The electrosurgical instrument includes at least two electrodes on the electrode probe that can be activated using an RF generator. The electrosurgical instrument is switchable between an ablation mode and a coagulation mode by changing the amount of active surface area. In particular, in the ablation mode, a relatively small surface area is active. Thus, for a given amount of power, the current density on or around the electrode is relatively high.

In the coagulation mode, the active surface area of the electrode is increased, thereby reducing the current density on or around the electrode(s) in the coagulation mode for a given amount of power. In the coagulation mode, the surface area can be sufficiently large and the current density sufficiently low that the device will coagulate instead of ablate while utilizing nearly all the power available in the ablation mode. By using a large percentage of the available power, the electrosurgical instrument of the invention exhibits relatively good ablation and coagulation capabilities using the same power source and probe.

The device of the present invention can be used effectively in either the ablation mode or the coagulation mode because the active surface area changes when the user switches between the ablation mode and the coagulation mode. This configuration is in contrast to existing devices where switching between an ablation mode and a coagulation mode is accomplished solely by reducing power. In such devices, the coagulation mode is operated under suboptimal conditions because a significant portion of the available power cannot be used in coagulation mode (i.e., increasing the power causes ablation, not increased coagulation). In contrast, with the device of the present invention, a relatively high power can be maintained when switching from the ablation mode to the coagulation mode because the active surface area increases. Thus, a comparatively larger amount of heat can be generated in the coagulation mode compared to the ablation mode using the same probe and the same RF generator. While not required, the device of the present invention can even be configured to allow an increase in power when switching from ablation mode to the coagulation mode, which is contrary to conventional thinking and practice.

In one embodiment of the invention, the electrosurgical instrument includes an elongate probe having a proximal end portion and a distal end portion. A first electrode is positioned on the distal end portion of the elongate probe, the first electrode is sized and configured to selectively ablate tissue in an ablation mode of the electrosurgical instrument at a given power input. A coagulation electrode is also positioned on the distal end portion but is electrically isolated from the first electrode. The coagulation electrode is sized and configured to selectively coagulate tissue, either alone or in combination with the first electrode, in a coagulation mode of the electrosurgical instrument at relatively high power input (e.g., the same as when the first electrode only is activated to cause ablation).

The electrosurgical instrument also includes a user operable input component, such as but not limited to a switch, that is electrically coupled to the first electrode and coagulation electrode. The user operable input component provides user selectable switching between the ablation mode and the coagulation mode. In the ablation mode the input component delivers power to the first electrode, and in the coagulation mode the input component delivers power to at least the coagulation electrode. In the coagulation mode the surface area that receives power is substantially greater than the surface that receives power in the coagulation mode. Therefore, for a given amount of power input, the device is configured to have a lower current density at the electrode(s) in the coagulation mode compared to the ablation mode.

In a preferred embodiment, the increased active surface area in the coagulation mode is provided by the device being configured to simultaneously deliver power to both the first electrode and the coagulation electrode in the coagulation mode. In this configuration, the first electrode is sized and configured to be an ablation electrode when used alone at a given power input. In the coagulation mode, the coagulation electrode is also active, thereby drawing away power to itself and thereby reducing the net effective power received by the first electrode while utilizing most, all, or even more power drive than what is required to the first electrode in the ablation mode. The first electrode and the coagulation electrode together provide an active surface area that causes coagulation of tissue using a much larger percentage of the power that could be used with just the first electrode in a coagulation mode. Simultaneous use of the first electrode and the coagulation electrode in the coagulation mode can be highly advantageous for achieving a compact probe that can be used in surgical procedures with tight size constraints.

Using relatively high power in the coagulation mode improves the efficiency and performance of the electrosurgical instrument in the coagulation mode. Nevertheless, the use of high power in the coagulation mode of dual mode electrosurgical instruments is contrary to the rationale used to operate many existing dual mode electrosurgical instruments, which typically reduce power to achieve coagulation and prevent ablation.

In an alternative embodiment, the first electrode can be inactivated in the coagulation mode. In this embodiment, the increased active surface area in the coagulation mode compared to the ablation mode can be provided by a coagulation electrode sized to provide the desired current density. This configuration also provides the benefits described above of using relatively high power in the coagulation mode. In addition, this embodiment can be advantageous where design restraints prevent optimal simultaneous use of the first electrode and the coagulation electrode in the coagulation mode.

The present invention also includes methods for operating an electrosurgical instrument. The method includes (i) providing an electrosurgical instrument including an elongate probe having a proximal end portion and a distal end portion, the distal end portion including a first electrode and a coagulation electrode; the electrosurgical instrument further including a user operable input component (e.g., a switch) for allowing a user to select between an coagulation mode and an ablation mode of the electrosurgical instrument; (ii) coupling the electrosurgical instrument to an RF generator that provides power to the electrosurgical instrument; (iii) selecting the ablation mode for the electrosurgical instrument using the input component and operating the electrosurgical instrument in the ablation mode; in the ablation mode, sufficient power is delivered to the first electrode to cause ablation of a patient's tissue; and (iv) selecting the coagulation mode for the electrosurgical instrument using the input component and operating the electrosurgical instrument in the coagulation mode; in the coagulation mode, sufficient power is delivered to the coagulation electrode (and optionally the first electrode) to cause coagulation of the tissue of the patient and, in the coagulation mode, a larger amount of electrode surface area is activated compared to the ablation mode. In a preferred embodiment, the method is carried out with an RF generator with a power output in a range from about 150 W to about 600 W, more preferably about 200 W to about 400 W.

The electrosurgical device may be configured to operate in a monopolar and/or bipolar fashion. In the case of monopolar operation, a grounding pad is typically attached to the patient's body to complete the electrical circuit. In bipolar operation, the return electrode is attached to the electrosurgical device itself, such as near the first (or ablation) electrode. In general, it is believed that ablation is more effective when operating in a bipolar mode, and coagulation is more effective when operating in a monopolar mode. Nevertheless, the electrosurgical device can be operated in monopolar or bipolar mode for either ablation or coagulation.

These and other advantages and features of the present invention will become more fully apparent from the following description and appended claims.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 2 is a perspective view of an exemplary embodiment of a distal portion of the probe of the electrosurgical instrument of FIG. 1;

FIG. 2A is a top view of the distal head portion of an alternative instrument including an electrode comprising a plurality of distinct surface areas each separated by an insulating material;

FIGS. 6A-6C illustrate various embodiments of electrode configurations according to the present invention;

FIGS. 7A-7B illustrate perspective views of an alternative electrode configuration at the distal end of an exemplary electrosurgical instrument.

DETAILED DESCRIPTION OF EXEMPLARY EMBODIMENTS

The present invention is directed to an electrosurgical instrument that can be selectively operated to alternatively perform ablation or coagulation. The electrosurgical instrument includes at least two electrodes on the electrode probe that can be activated using an RF generator. The electrosurgical instrument is switchable between an ablation mode and a coagulation mode by changing the effective active surface area. In particular, in the ablation mode, a relatively small electrode surface area is activated. Thus, for a given power input, the current density on or near the ablation electrode is relatively high. In the coagulation mode, the active surface area is increased, thereby reducing the current density on or near the coagulation electrode(s) in the coagulation mode for the given power input.

Figure 1:
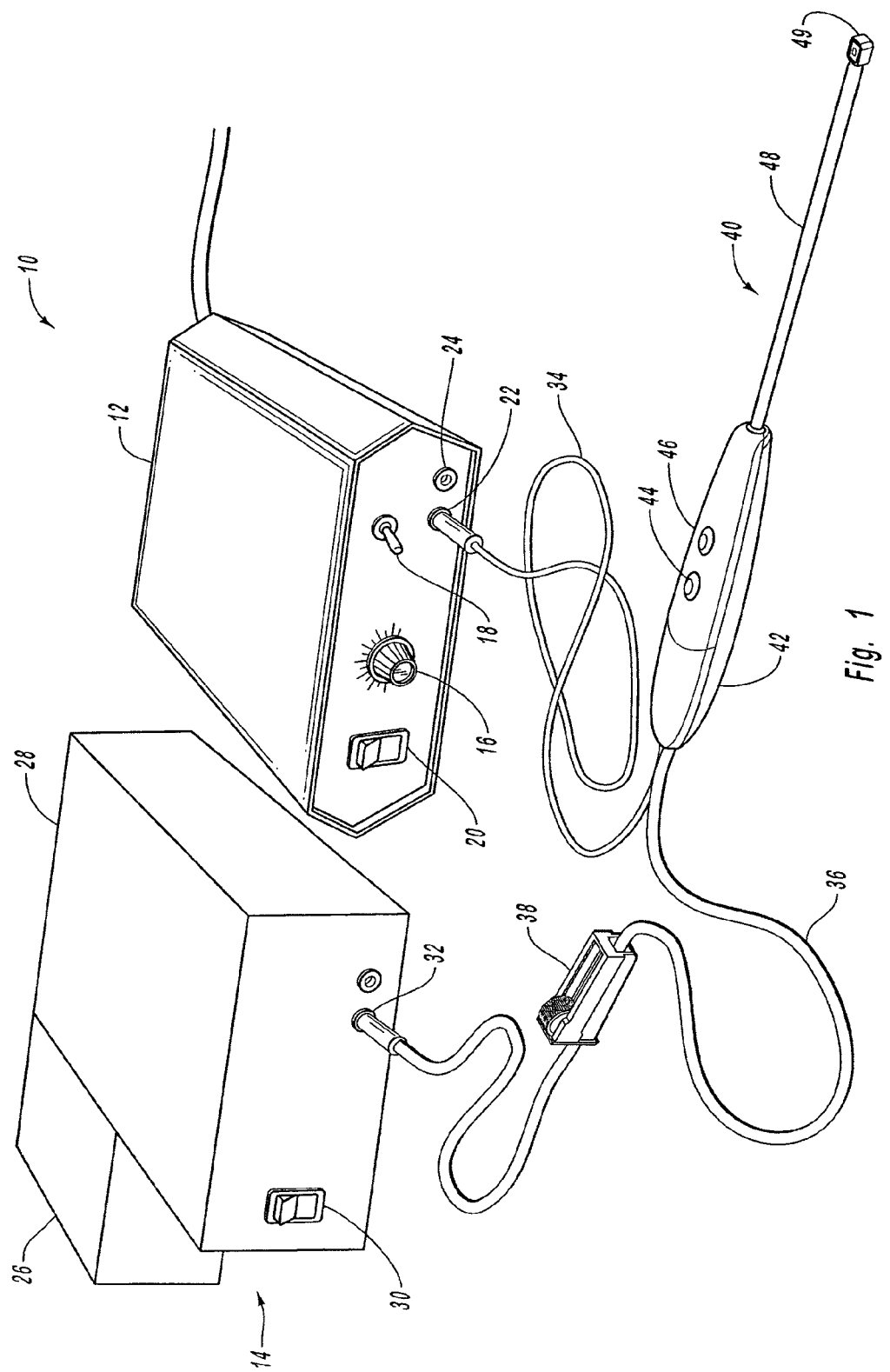
FIG. 1 is a perspective view of an electrosurgical instrument including a radio frequency generator, an aspirator, and an electrosurgical probe according to an embodiment of the invention.

FIG. 1 shows an exemplary electrosurgical system according to one embodiment of the invention. The electrosurgical system 10 includes an electrosurgical probe 40 that is electrically coupled to an electrosurgical generator 12 and an aspirator 14.

Electrosurgical generator 12 is configured to generate radio frequency ("RF") wave forms. Generator 12 can generate power useful for ablating tissue and/or coagulating tissue. In one embodiment, generator 12 includes standard components, such as dial 16 for controlling the frequency and/or amplitude of the RF energy, a switch 18 for changing the type of waveform generated (e.g., between cut and coag), a switch 20 for turning the generator on and off, and an electrical port 22 for connecting the electrosurgical instrument 40. Generator 12 also includes port 24 for connecting an electrical ground or a return electrode. It will be appreciated that generator 12 can be designed for use with bipolar electrosurgical instruments instead of, or in addition to, monopolar devices.

Aspirator 14 includes a pump 26, a reservoir 28, an on/off switch 30, and an aspirator port 32. Pump 26 provides negative pressure for aspirating fluids, gasses, and debris through electrosurgical instrument 40. Aspirated fluids and debris can be temporarily stored in reservoir 28. In another embodiment, electrosurgical instrument 40 is connected to wall suction. When using wall suction, canisters or other reservoirs are placed in the suction line to collect aspirated tissue and fluids. Those skilled in the art will recognize that many different configurations of generator 12 and aspirator 14 can be used in the present invention.

Electrosurgical instrument 40 is depicted as an elongate probe and includes a power cord 34 for electrically connecting instrument 40 to generator 12 through electrical port 22. Extension tubing 36 provides a fluid connection between instrument 40 and aspirator 14. A flow control device 38 allows a practitioner to vary the rate of aspiration through instrument 40.

The electrosurgical instrument 40 includes a proximal end portion 42 and a distal end portion 48. In one embodiment, proximal end portion 42 can provide a handle for instrument 40. Distal end portion 48 of probe 40 includes an electrode head 49, which includes a plurality of electrodes.

Figure 1A:
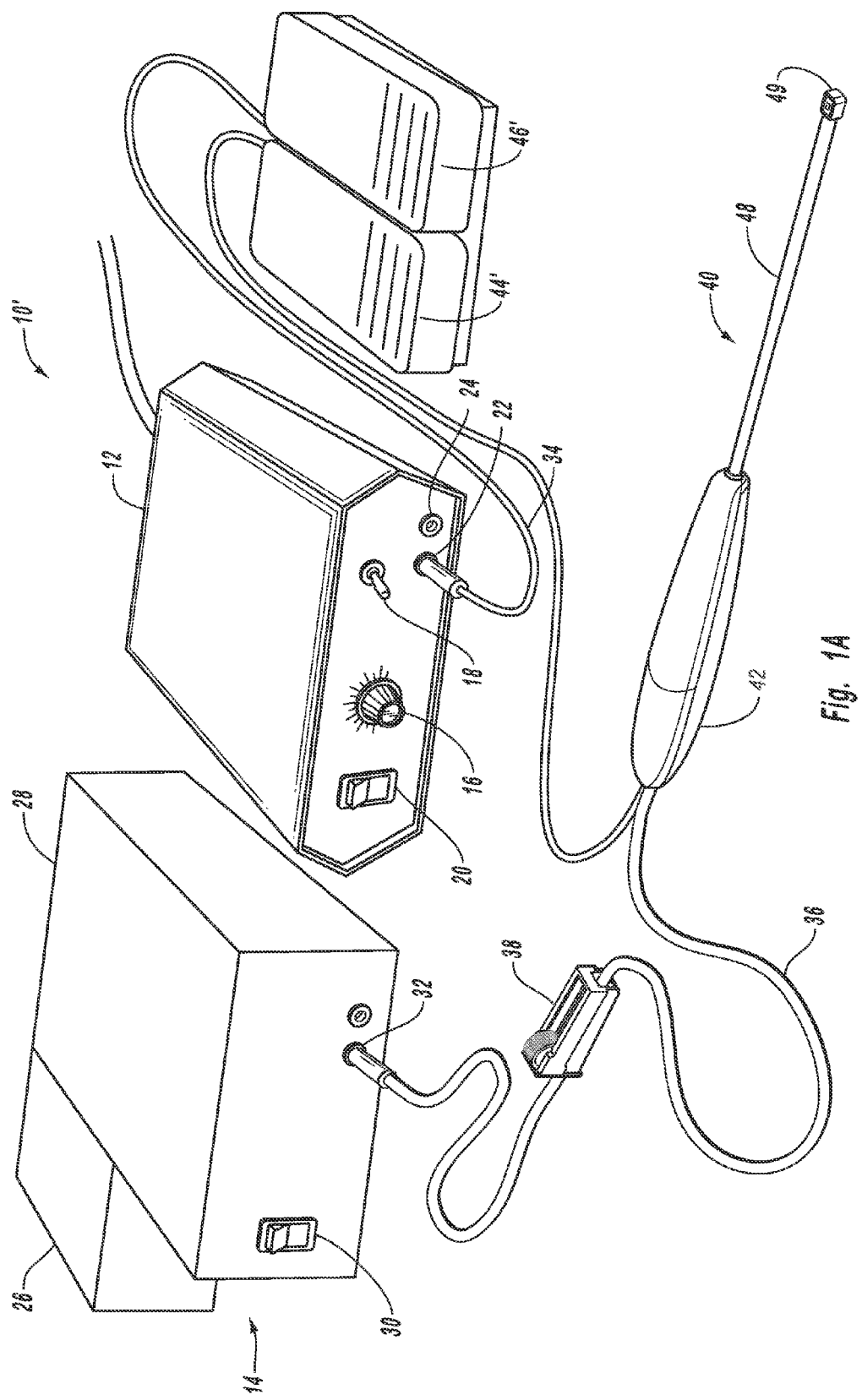
FIG. 1A is a perspective view of an alternative system including a foot pedal.

FIG. 1A illustrates an exemplary system 10' including a foot pedal as an alternative to the push button switches 44 and 46 on the proximal portion of the instrument 42 as shown in FIG. 1. For example, system 10' includes foot pedals 44' and 46', which may function similar to push buttons 44 and 46. Such an alternative configuration may advantageously be provided to suit the preference of the practitioner.

Instrument 40 can be used for selectively ablating or coagulating tissue in a patient. Buttons 44 and 46 on the proximal end portion 42 can be used to switch instrument 40 between a first operational mode for ablating tissue and a second operational mode for coagulating tissue.

Instrument 40 includes at least two active electrodes that are physically and electrically configured to provide a larger active surface area when instrument 40 is in the coagulation mode compared to the active surface area when instrument 40 is in the coagulation mode. FIG. 2 illustrates an exemplary embodiment of an electrode configuration that provides a greater active surface area in a coagulation mode compared to an ablation mode. As shown in FIG. 2, instrument 40 includes a first electrode 50 and a coagulation electrode 52 on distal end portion 48. First electrode 50 and coagulation electrode 52 are conductive elements such as a metal or other suitable material for conducting a current. First electrode 50 and second electrode 52 are electrically isolated from one another by insulating material 54. In this embodiment, electrode 50 and 52 are concentric with one another. However, the invention includes electrode configurations where the first electrode and the coagulation electrode are not concentric, as described more fully below with respect to FIGS. 6A-6D and 7A-7B. An outer insulative material 58 provides a protective covering on the distal end portion 48 of instrument 40, while leaving electrodes 50 and 52 exposed.

An aspiration lumen 56 can be positioned within electrode 52. Aspiration lumen 56 can be used with aspirator 14 (FIG. 1) to withdraw fluids and debris from the surgical site during ablation. In a preferred embodiment, aspiration lumen is located within second electrode 52 to provide some distance between first electrode 50 and aspiration lumen 56. This distance between first electrode 50 and aspiration lumen 56 can be beneficial since aspirating fluids tends to have a cooling effect on adjacent surroundings and cooling can be undesirable for achieving a plasma in the ablation mode. However, those skilled in the art will recognize that an aspiration lumen 56 is not required to carry out the invention and that the aspiration lumen 56 can be located in various places on instrument 40, if desired.

First electrode 50 is configured to provide ablation when instrument 40 is in the ablation mode. Electrodes that are configured for ablation have a surface area that can create a plasma in an aqueous medium when power from power source 12 is delivered to the electrode. The particular configuration of the first electrode that allows ablation to be achieved will depend on the power for which the instrument 40 is designed to operate. In one embodiment, instrument 40 is designed to operate within a range from about 150 W to about 500 W, more preferably about 200 W to about 400 W. For a power rating of about 400 W, the active surface area can be in a range from about 3 $mm^2$ to about 30 $mm^2$, more preferably about 5 $mm^2$ to about 25 $mm^2$, and most preferably about 7 $mm^2$ to about 20 $mm^2$.

Coagulation electrode 52 is configured to perform coagulation in a tissue, either alone or in combination with one or more auxiliary electrodes (e.g., first electrode 50). Electrodes that are configured for coagulation have an active surface area that does not create a plasma in an aqueous medium when power from power source 12 is delivered to the electrode, but have sufficiently small surface area such that power from power source 12 will generate sufficient heat to cause coagulation in a tissue. For example, for a power rating of about 400 W, the active surface area during coagulation can be in a range from 10 $mm^2$ to about 50 $mm^2$. The coagulation electrode 52 is greater in size than the first electrode, which allows coagulation to occur instead of ablation. In one embodiment, the coagulation electrode that is active during coagulation is at least 10% larger in surface area than the surface area of the first electrode, alternatively at least 15% larger, 25% larger, or even 50% larger in surface area. Those skilled in the art are readily familiar with selecting suitable power levels and electrode surface areas to achieve coagulation in the tissue of a patient. The coagulation electrode 52 also has a surface area that is smaller than the return electrode (not shown) (e.g., in a bipolar device). In one embodiment the surface area of the coagulation electrode is at least 10% smaller than the surface area of the return electrode, alternatively at least 15% smaller, 25% smaller, 50%, or even 75% smaller in surface area.

The surface area required to configure an electrode for ablation or coagulation will depend on the power to be delivered to the device. It is customary in the art to provide power generators that allow a practitioner to adjust the power. For purposes of this invention, the determination as to whether the electrode 50 is configured for ablation and electrode 52 is configured for coagulation is made in reference to a single power setting (i.e., first electrode 50 ablates at a design power and coagulation electrode 52 alone or in combination with first electrode 50 coagulates at the same design power). However, it will be understood that in use a practitioner may chose to select different power settings for the ablation mode and coagulation mode, so long as the power settings provide ablation when operating in an ablation mode and coagulation when operating in a coagulation mode.

Electrodes 50 and 52 are configured to allow a user to selectively operate instrument 40 in a coagulation mode or an ablation mode. The user selects between the two operational modes by actuating a user operable input component (e.g., a switch). The user operable input component can be any type of mechanical or electrical input device that causes a change in the amount of active surface area on instrument 40 so as to cause electrode 50 and/or electrode 52 to operate under coagulation conditions or alternatively to operate under ablation conditions. For example, the amount of active surface area may be increased for coagulation mode by activating first electrode 50 during ablation and activating coagulation electrode 52 during coagulation. Coagulation electrode may 52 have a greater surface area than first electrode 50. Alternatively, both electrodes 50 and 52 may be active during coagulation, providing an even greater surface area for coagulation.

In one embodiment, the user input component can be a mechanical switch. Examples of mechanical switches include push button switches, lever actuated switches, foot pedal switches, etc. Those skilled in the art will recognize that there are many different types of switches that can be employed in the present invention as a user operable input device. Furthermore, those of skill in the art will recognize that the user input component (e.g., a switch) may not switch the full voltage applied by the generator intended for delivery to electrodes 50 and/or 52. Rather, the user input component may rely on switching a relatively smaller voltage within instrument 40, which provides a signal (e.g., to generator 12) to switch the full employed voltage. For example, the switching voltage within instrument 40 may only be about 12 volts, while the full voltage switched and delivered to electrodes 50 and/or 52 may be much greater (e.g., about 400 volts)

In the embodiment shown in FIG. 2, the first electrode and the coagulation electrode each comprise a continuous surface area. In an alternative configuration, one or more of the included electrodes may comprise a plurality of distinct surface areas each separated by an insulating material. An example of such a configuration is shown in FIG. 2A, which shows a close up of an alternative electrode head 49' similarly including a first electrode 50', a coagulation electrode 52', insulating material 54', and an aspiration lumen 56'. In the illustrated example, first electrode 50' comprises a plurality of distinct surface areas separated by insulating material 54'. Although illustrated with only first electrode 50' comprising a plurality of distinct surface areas, it will be understood that coagulation electrode 52' could also or alternatively comprise a plurality of distinct surface areas.

Figure 3A:
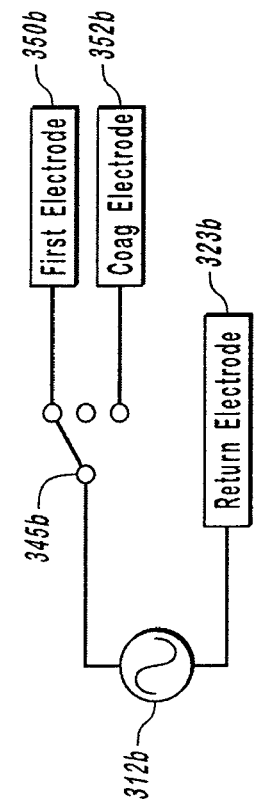
FIG. 3A is an exemplary circuit diagram of an electrosurgical instrument according to the present invention.
Figure 3B:
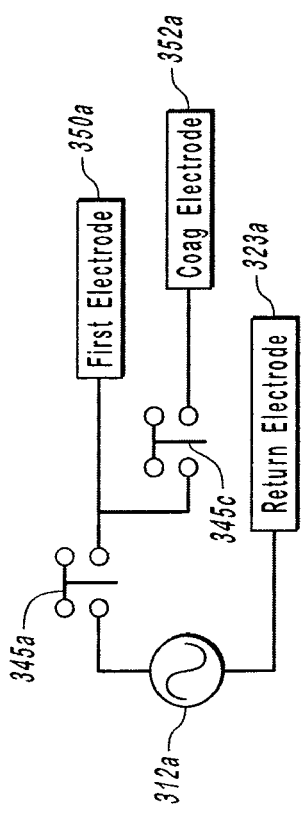
FIG. 3B is an alternative circuit diagram of an electrosurgical instrument according to the present invention.

When actuated, the user operable input component causes power to be delivered either to one or both of first electrode 50 and coagulation electrode 52. FIGS. 3A and 3B are circuit diagrams illustrating exemplary electrical configurations that allow a user to selectively switch between a coagulation mode and an ablation mode by changing the active surface area to achieve the two different modes. FIG. 3A illustrates an electrical configuration where first electrode 350a performs ablation when instrument 40 is in an ablation mode and coagulation electrode 352a, together with first electrode 350a, performs coagulation when instrument 40 is in a coagulation mode.

In FIG. 3A, a power source 312a is electrically coupled to an on/off switch 345a and a return electrode 323a. On/off switch 345a is electrically coupled to first electrode 350a and a selector switch 345c. Selector switch 345c is electrically coupled to coagulation electrode 352a. FIG. 3A illustrates instrument 40 in an off position. To achieve the ablation mode, a user actuates on/off switch 345a, which delivers current from RF generator 312a to first electrode 350a. The circuit is completed by current traveling through tissue or fluids within a patient to return electrode 323a. The return electrode 323a may be attached to the patient (i.e., for monopolar operation) or near one or both of the electrodes (i.e., for bipolar operation). With on/off switch 345a actuated and selector switch 345c deactivated, coagulation electrode 352a is off (i.e., inactive). Thus, the entire active electrode surface area is provided by first electrode 350a. First electrode 350a has a surface area suitable for carrying out ablation when activated by RF generator 312a with selector switch 345c in the off position.

To achieve the coagulation operational mode, the user actuates selector switch 345c, which then delivers a portion of the current to coagulation electrode 352a, thereby activating the surface of coagulation electrode 352a. The circuit for both the first electrode 350a and the coagulation electrode 352a are completed through fluids or tissue electrically coupled to return electrode 323a. In the coagulation mode, current is shared between first electrode 350a and coagulation electrode 352a, thereby reducing the current to first electrode 350a (compared to the current delivered to first electrode 350a when operating in ablation mode). The active electrode surface area in the coagulation mode is the sum of the active area on the first electrode 350a and the coagulation electrode 352a, which is greater than the active electrode surface area of the first electrode 350a by itself when operating in the ablation mode. The increased electrode surface area results in a sufficiently lower current density to avoid generating a plasma, but sufficiently high current density to cause coagulation.

FIG. 3B is a circuit diagram of a probe according to the invention that has a pole switch 345b that allows current to be selectively delivered to first electrode 350b or coagulation electrode 352b. RF generator 312b is electrically coupled to pole switch 345b and return electrode 323b (e.g., as described relative to FIG. 3A). Pole switch 345b can be switched by a user between three positions which correspond to ablation mode, coagulation mode, and off. Pole switch 345b is shown positioned in the ablation mode. In this configuration, current from RF generator is delivered to only first electrode 350b. Actuation by a user can position pole switch 345b in a middle position, in which case the probe is turned off. Further movement of pole switch 345b to the bottom position activates coagulation electrode 352b, but not first electrode 350b. Coagulation electrode 352 has a greater active electrode surface area than ablation electrode 350b. Consequently, the current density on coagulation electrode 352b is less compared to the current density of first electrode 350b when pole switch 345b is positioned in the ablation mode. The lower current density in the coagulation mode results in coagulation rather than ablation, even if the power output of RF generator 312*b* is the same, greater, or less than the power output with pole switch 345*b* positioned in the ablation mode.

In the embodiment shown in FIG. 3B, the coagulation electrode 352*b* will typically have a larger surface area than the ablation electrode 350*b*. However, in the embodiment shown in FIG. 3A, the surface area of the coagulation electrode 352*a* can be the same, larger, or smaller than the first electrode 350*a*, so long as the total active electrode surface area in coagulation mode is larger than the active electrode surface area in ablation mode.

Figure 4A:
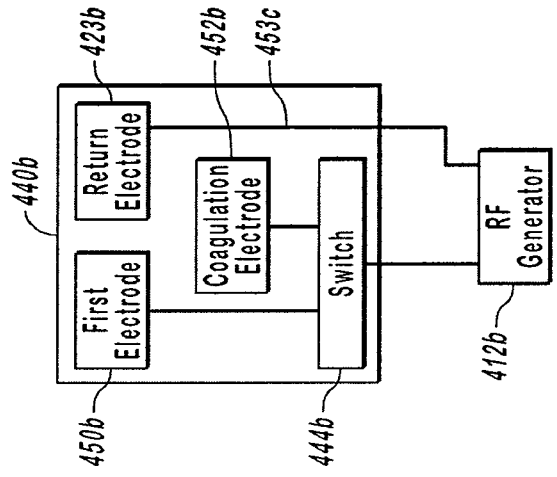
FIG. 4A is a schematic diagram of the electrode configuration of an exemplary monopolar instrument according to an embodiment of the present invention.
Figure 4B:
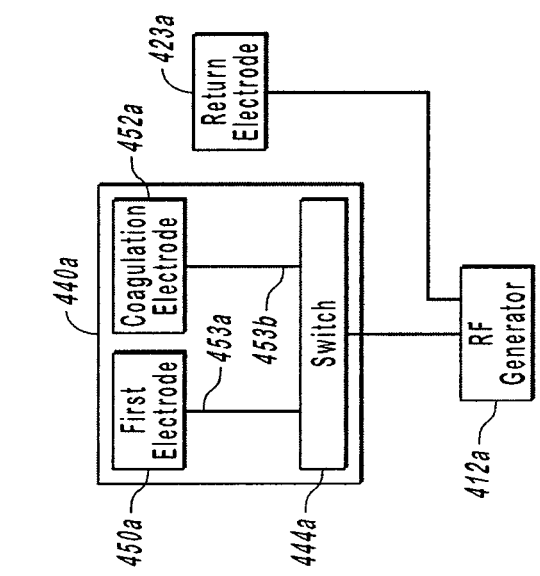
FIG. 4B is a schematic diagram of the electrode configuration of a bipolar instrument according to another embodiment of the present invention.

FIGS. 4A and 4B are schematic diagrams showing the incorporation of a switch and electrodes into a probe or instrument. FIGS. 4A and 4B illustrate monopolar and bi-polar electrode configurations, respectively. In FIG. 4A, a probe 440*a* includes a first electrode 450*a*, a coagulation electrode 452*a*, and a switch 444*a*. Probe 440*a* is electrically coupled to RF generator 412*a*. A return electrode 423*a* is electrically coupled to RF generator 412*a*. In this embodiment, return electrode 423*a* is not incorporated into probe 440*a*. Return electrode 423*a* is therefore placed on the body of a patient to provide a completed electrical circuit. The monopolar configuration illustrated in FIG. 4A includes two leads 453*a*, 453*b* that electrically couple switch 444*a* with first electrode 450*a* and coagulation electrode 452*a*. This monopolar configuration can be advantageous because it eliminates the complexity involved with incorporating additional electrodes into the probe, which can be very small (e.g., the distal head end of the probe may be about 4 mm in length).

FIG. 4B illustrates a bipolar configuration where probe 440*b* includes a first electrode 450*b*, a coagulation electrode 452*b*, and a return electrode 423*b* electrically coupled to RF generator 412*b*. Return electrode 423*b* is incorporated into probe 440*b* and electrically coupled to switch 444*b* through a lead 453*c*. Placing return electrode 423*b* on probe 440*b* can be advantageous because it reduces the amount of current that travels through the patient during operation and it eliminates the need to have a separate electrical cord or wire properly attached to the patient.

While FIGS. 4A and 4B illustrate monopolar and bipolar configurations, the invention is not limited to separate monopolar and bipolar configurations and additional separate electrodes can be placed on the probe, provided there is sufficient surface area. Alternatively, the device can be configured to selectively operate in either monopolar mode (e.g., during coagulation or ablation) or bipolar mode (e.g., during ablation).

While switches 444*a* and 444*b* have been shown as incorporated into probe 440*a* and 440*b*, respectively, those skilled in the art will recognize that one or more switches can be external to the probe. For example, one or more switches can be incorporated into a foot pedal that is electrically coupled to the RF generator and probe 440*a* or 440*b*.

Figure 5:
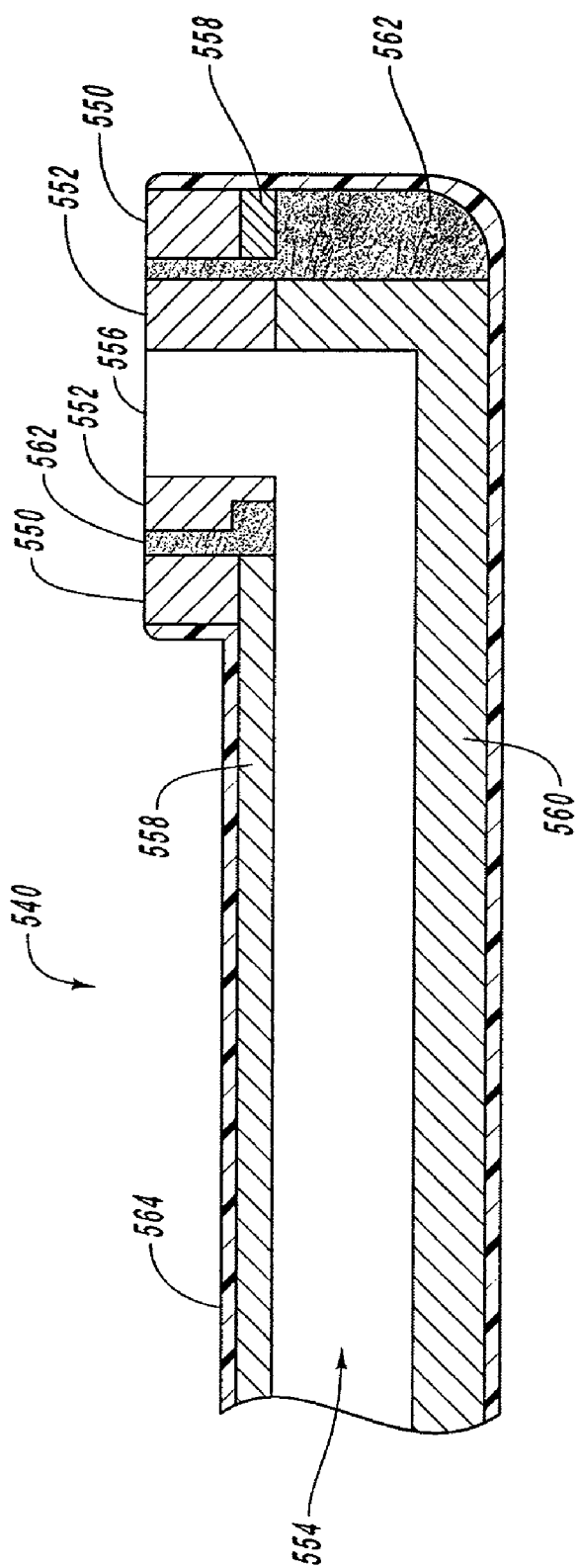
FIG. 5 is a cross sectional view of an exemplary monopolar electrosurgical instrument according to an embodiment of the invention.

The present invention encompasses devices having a wide variety of configurations. Typically the instrument or probe will have a hollow tube with electrical leads incorporated into the tubing and leading to a distal end. FIG. 5 illustrates a cross section of an exemplary monopolar probe 540 according to one embodiment of the invention. Probe 540 is a cross section of an electrode head substantially similar to that shown in FIG. 1. Probe 540 forms an elongate tube having an aspiration lumen 554 that leads to an aspiration opening 556 at a distal end of probe 540. Probe 540 includes a first electrical lead 558 that is electrically coupled to first electrode 550. First electrode 550 may be configured to carry out ablation when activated. Second electrical lead 560 is electrically coupled to second electrode 552. Second electrode 552 may be configured to cause coagulation in a coagulation mode of the device. First electrode 550 and second electrode 552 are electrically isolated by insulative material 562, 564. Similarly, leads 558 and 560 are electrically isolated from one another. Those skilled in the art are familiar with configuring electrodes and insulators to provide electrical isolation while allowing current from the RF generator to power the electrode.

The particular configuration of the first electrode and second electrode can be varied. For example the first electrode and second electrode can be concentric rectangles as shown in FIG. 1. FIGS. 6A-6D and 7A-7B illustrate alternative configurations of electrodes. FIG. 6A illustrates an electrode head 649*a* with circular concentric electrodes. Electrode head 649*a* includes a first electrode 650*a*, a second electrode 652*a*, and an insulative material 654*a* electrically isolating the two electrodes. An optional aspiration lumen 656*a* is positioned within second electrode 652*a*. Although FIG. 6A shows the first electrode 650*a* positioned outside of the second (e.g., coagulation) electrode 652*a*, those skilled in the art will recognize that the concentric electrodes can be reversed such that the coagulation electrode 652*a* is positioned outside of the first electrode 650*a*.

FIG. 6B illustrates an electrode configuration that is not concentric. In this embodiment, an electrode head 649*b* includes a first electrode 650*b* that is configured for ablation and a second electrode 652*b* that is configured to coagulate (alone or in combination with first electrode 650*b*). Insulative material 654*b* electrically isolates first electrode 650*b* from second electrode 652*b*. An optional aspiration lumen 656*b* is positioned within second electrode 652*b*.

FIG. 6C illustrates a bi-polar electrode head 649*c*. Bi-polar electrode head 649*c* includes a first electrode 650*c* that is concentric to a second (e.g., coagulation) electrode 652*c*, which is concentric to aspiration lumen 656*c*. Electrode head 649*c* also includes a return electrode 623*c*. Return electrode 623*c*, first electrode 650*c*, and coagulation electrode 652*c* are electrically isolated using an insulative material 654*c*. Return electrode 623*c* has a sufficiently large surface area that very little heat is generated from current passing through it, such that return electrode 623*c* does not cause coagulation or result in a burn to the patient.

FIGS. 7A-7B illustrate perspective views of another alternative electrode head 749. Electrode head 749 includes a first electrode 750 on a first side of head 749, while a second (or coagulation) electrode 752 is disposed on an opposite side of head 749 relative to the first electrode 750. The first electrode 750 is perhaps best seen in FIG. 7A, while FIG. 7B perhaps offers the best view of second (or coagulation) electrode 752. In the embodiment of FIGS. 7A-7B, first electrode 750 can be planar and two-dimensional. Coagulation electrode 752 is illustrated as being nonplanar and three-dimensional, so that it comprises a substantially bell-shaped or hemispherical protrusion extending outwardly from the distal head portion 749 of the probe. Of course, alternative planar configurations such as that illustrated in FIG. 2 are also possible. Electrode head 749 can be formed from an insulating material 754 to electrically isolate first electrode 750 and coagulation electrode 752. In the illustrated embodiment, an aspiration lumen is centrally disposed on the side of first electrode 750, so that first electrode 750 forms a concentric circle around aspiration lumen 756.

Electrode head 749 may also optionally include one or more return electrodes 723. In the illustrated example, return electrode 723 is disposed on another side of electrode head 749, between the opposing sides that include first electrode 750 and second (or coagulation) electrode 752, respectively. In order to provide sufficient surface area to return electrode 723, return electrode 723 may also cover at least a portion of top and bottom surfaces of the probe, adjacent to electrodes 750 and 752, as illustrated. Preferably, return electrode 723 has a surface area that is at least about twice as large as the surface area of coagulation electrode 752. More preferably, the surface area of return electrode is at least about four times as large as the surface area of coagulation electrode 752.

Of course, a monopolar example device may omit the return electrode 723, instead using a return electrode separate from the electrosurgical instrument and that is electrically coupled to the patient during use. According to one embodiment, a bipolar configuration including a return electrode 723 may be employed during ablation, as such a configuration is perceived to provide increased current density on or around the first electrode 750. When operating in a coagulation mode, a monopolar configuration may be particularly preferred as the decreased current density on or around coagulation electrode 752 of such a configuration is believed to provide more diffuse heat that is drawn toward the tissue for improved coagulation of the tissue. Any of the above described monopolar configurations may be modified so as to be bipolar. Similarly, any of the above described bipolar configurations may be modified so as to be monopolar.

Figure 8A:
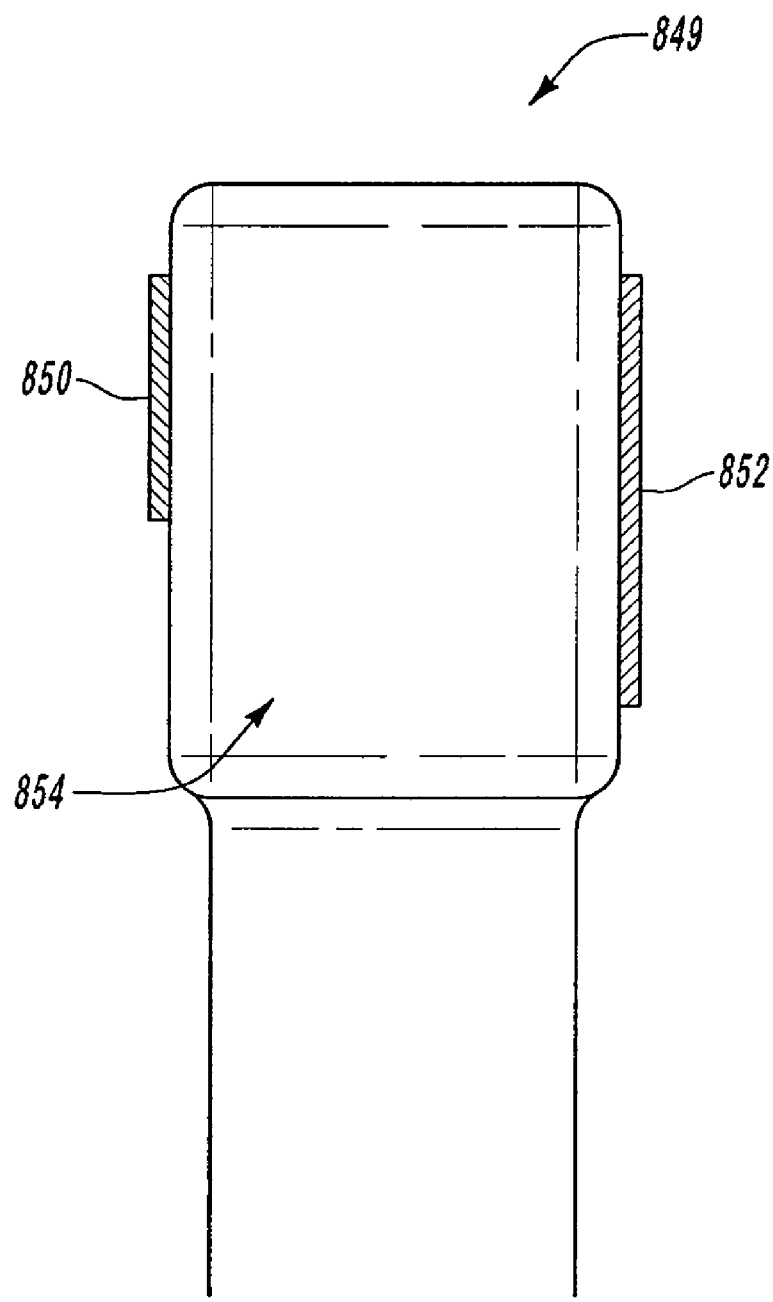
FIGS. 8A-8B illustrate another alternative electrode configuration.
Figure 8B:
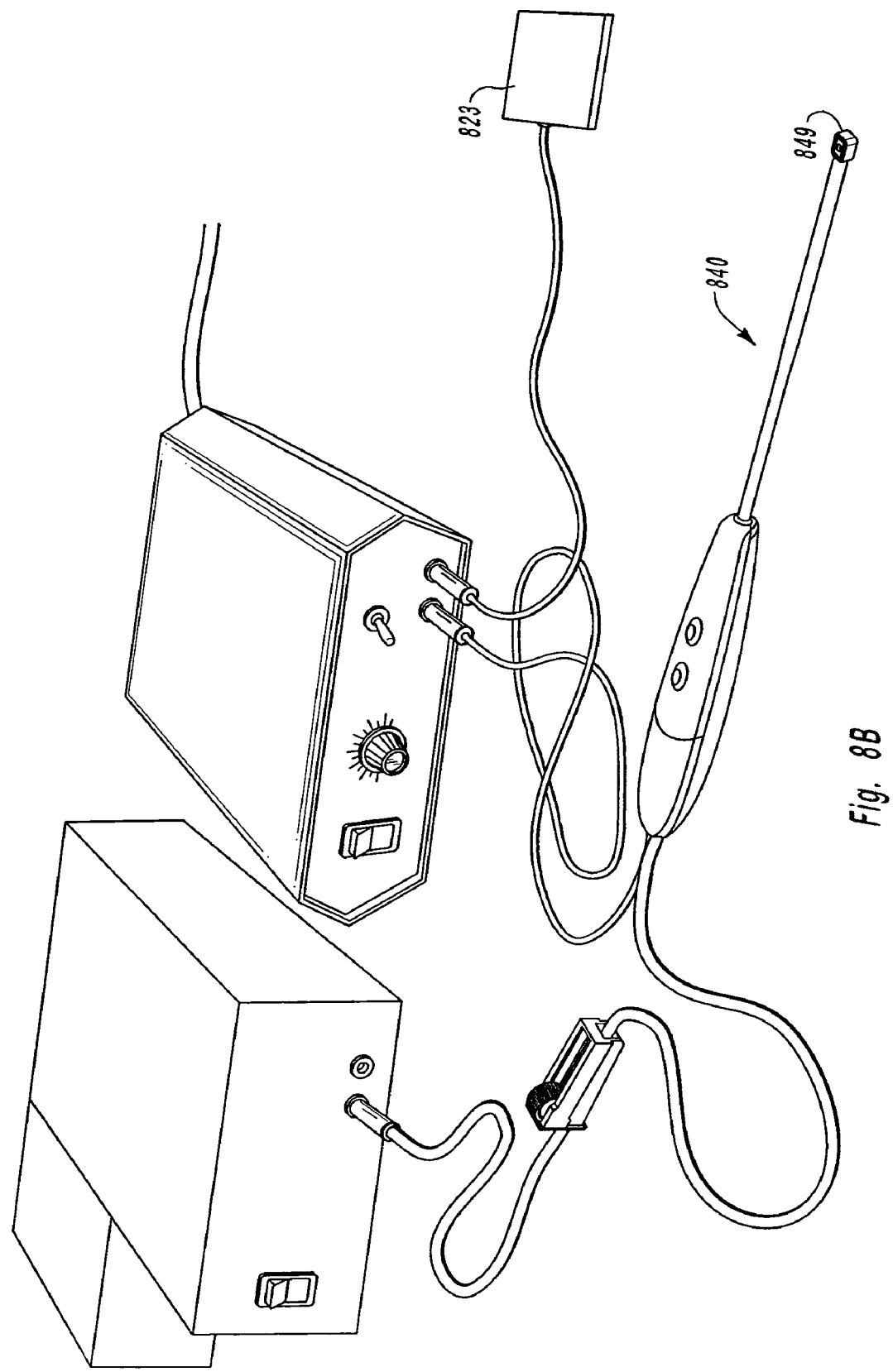

FIGS. 8A and 8B illustrate another alternative electrode head 849 that may operate in a bipolar mode when used for ablation and that may operate in a monopolar mode when used for coagulation. FIG. 8A shows a close-up perspective view of the head 849 of the instrument. Head 849 includes a first electrode 850 on a first side of head 849, while a second electrode 852 is disposed on an opposite side of head 849 relative to the first electrode 850. Electrode head 849 can be formed from an insulating material 854 to electrically isolate first electrode 850 and second electrode 852. An aspiration lumen may also be included (e.g., centrally disposed on the side of first electrode 850, so that first electrode 850 forms a concentric circle around the aspiration lumen (not shown)). When used in an ablation mode, second electrode 852 may serve as a return electrode. When used in an ablation mode, second electrode becomes a coagulation electrode, and a separately provided return electrode (e.g., a grounding pad) is attached to the patient's body to complete the electrical circuit. FIG. 8B shows a larger perspective view of the instrument 840, including separately provided grounding pad return electrode 823 connected to the RF generator.

Use of the coagulation electrode 852 as a return electrode during ablation mode is helpful in maximizing use of the small available on head 849 (e.g., which may only measure about 4 mm in length). Using coagulation electrode 852 as the return electrode during ablation provides for bipolar operation without requiring the location of another electrode on the small surface area available on head 849. This is possible because the power delivered during an ablation procedure may typically be less than that provided during a coagulation procedure, so that the surface area provided by the second electrode 852 is sufficient to serve as a return electrode. For example, the power delivered during an ablation procedure may be about 200 W, while the power delivered during a coagulation procedure may typically be greater (e.g., about 400 W).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An electrosurgical instrument for selectively ablating or coagulating tissue of a patient at a surgical site, the electrosurgical instrument being switchable between an ablation mode and a coagulation mode, the electrosurgical instrument comprising:
  an elongate probe having a proximal end and a distal end;
  a first electrode positioned on a first surface at the distal end of the elongate probe, the first electrode having a first surface area so as to generate a first current density sufficient to ablate tissue when a first amount of power is delivered to the first electrode during operation of the electrosurgical instrument in an ablation mode;
  a coagulation electrode positioned at a second opposing surface of the distal end of the elongate probe and so as to be electrically isolated from the first electrode, the coagulation electrode having a second surface area greater than the first surface area so as to generate a second current density that is sufficient to coagulate tissue when a second amount of power that is greater than the first amount of power is delivered to the coagulation electrode during operation in a coagulation mode; and
  a user operable input component or switch electrically coupled to the first electrode and to the coagulation electrode for selectively delivering power from a power generator to one or both of the first electrode or the coagulation electrode, the user operable input component or switch providing user selectable switching between the ablation mode and the coagulation mode, wherein
    when the electrosurgical instrument operates in the ablation mode, the user operable input component or switch selectively causes the first amount of power to be delivered only to the first electrode and not to the coagulation electrode so as to generate the first current density at the first electrode sufficient to ablate tissue, and
    when the electrosurgical instrument operates in the coagulation mode, the user operable input component or switch selectively causes the second amount of power to be delivered to at least the coagulation electrode so as to generate the second current density at the coagulation electrode and optionally also at the first electrode sufficient to coagulate tissue.

2. An electrosurgical instrument as in claim 1, in which, in the coagulation mode, the input component or switch causes a first portion of the second amount of power to be delivered to the first electrode and a second portion of the second amount of power to be delivered to the coagulation electrode, thereby configuring the first electrode for coagulation while the electrosurgical instrument operates in the coagulation mode.

3. An electrosurgical instrument as in claim 1, further comprising an aspiration lumen at the distal end of the elongate probe.

4. An electrosurgical instrument as in claim 1, wherein the first electrode and the coagulation electrode comprises a plurality of distinct surface areas each separated by an insulating material.

5. An electrosurgical instrument as in claim 1, wherein a total electrode surface area that is activated when operating the electrosurgical instrument in the coagulation mode is at least 10% larger than when operating the electrosurgical instrument in the ablation mode.

6. An electrosurgical instrument as in claim 5, wherein the total electrode surface area that is activated when operating the electrosurgical instrument in the coagulation mode is at least 25% larger than when operating the electrosurgical instrument in the ablation mode.

7. An electrosurgical instrument as in claim 1, wherein the elongate probe is operable in a monopolar mode.

8. An electrosurgical instrument as in claim 7, further comprising a return electrode separate from the elongate probe that is sized and configured to be attached to an external part of the body of a patient.

9. An electrosurgical instrument as in claim 1, wherein the elongate probe further comprises a return electrode positioned anywhere along or in proximity to the distal end of the elongate probe so as to provide an electrical return to a power source for the elongate probe and in order for the electrosurgical instrument to be operable in a bipolar mode.

10. An electrosurgical instrument as in claim 1, wherein the user operable input component includes a switch that is incorporated into the proximal end of the elongate probe.

11. An electrosurgical instrument as in claim 1, wherein the coagulation electrode has a rounder surface with fewer or no sharp edges compared to the first electrode.

12. An electrosurgical instrument as in claim 1, wherein the coagulation electrode is nonplanar and comprises a protrusion extending outwardly from the distal end of the elongate probe.

13. An electrosurgical system, comprising: the electrosurgical instrument as in claim 1, and an RF generator, wherein the user operable input component includes a foot pedal electrically coupled to the RF generator.

14. A method for selectively ablating or coagulating tissue at a surgical site, comprising:
  (i) providing an electrosurgical instrument comprised of multiple electrically isolated electrodes that are independently activatable for selectively varying total active electrode surface area so as to vary electrode current density and a user operable switch for allowing a user to select between a coagulation mode and an ablation mode by selectively varying total active electrode surface area so as to vary current density;
  (ii) coupling the electrosurgical instrument to an RF generator, the RF generator providing power to the electrosurgical instrument;
  (iii) selecting the ablation mode for the electrosurgical instrument using the user operable switch and operating the electrosurgical instrument in the ablation mode, the user operable switch causing a first amount of power to be delivered from the RF generator to a subset of the electrodes so as to generate a total active electrode surface area having a current density sufficient to cause tissue ablation at the surgical site; and
  (iv) selecting the coagulation mode for the electrosurgical instrument using the user operable switch and operating the electrosurgical instrument in the coagulation mode, the user operable switch causing a second amount of power that is greater than the first amount of power to be delivered to a greater total active electrode surface area while providing a lower current density as when operating in the ablation mode so as to cause tissue coagulation at the surgical site.

15. A method as in claim 14, wherein operating the electrosurgical instrument in the coagulation mode comprises delivering a portion of the power from the RF generator to a first electrode and a second portion of the power to a second electrode.

16. A method as in claim 14, wherein the power provided by the RF generator is in a range from 150 W to 600 W.

17. A method as in claim 14, wherein the power provided by the RF generator is in a range from about 200 W to about 400 W.

18. A method as in claim 14, wherein step (iii) is performed prior to step (iv).

19. A method as in claim 14, wherein step (iv) is performed prior to step (iii).

20. A method as in claim 14, wherein the power provided by the RF generator is greater in step (iv) than in step (iii).

21. A method as in claim 14, wherein the electrosurgical instrument includes a first dedicated ablation electrode having sharp edges and a second dedicated coagulation electrode having rounded edges.

22. A method as in claim 14, wherein the greater total active electrode surface area when operating in the coagulation mode is at least 10% larger than the total active electrode surface area when operating in the ablation mode.

23. A method as in claim 14, further comprising aspirating fluids through a lumen while operating the electrosurgical instrument in the ablation mode.

24. A method as in claim 14, wherein the electrodes comprise a dedicated ablation electrode that is activated while operating in the ablation mode and a dedicated coagulation electrode that operates as a return electrode but does not itself ablate tissue while operating in the ablation mode.

25. An electrosurgical instrument for selectively ablating or coagulating tissue of a patient at a surgical site, the electrosurgical instrument being switchable between an ablation mode and a coagulation mode, the electrosurgical instrument comprising:
  an elongate probe having a proximal end and a distal end;
  a first electrode positioned on a first surface of the distal end of the elongate probe, the first electrode having at least one sharp edge and a first surface area so as to generate a first current density sufficient to ablate tissue when a first amount of power is delivered to the first electrode during operation of the electrosurgical instrument in an ablation mode;
  a coagulation electrode positioned at a second opposing surface of the distal end of the elongate probe and so as to be electrically isolated from the first electrode, the coagulation electrode having a rounded surface with no sharp edges and a second surface area greater than the first surface area so as to generate a second current density that is less than the first current density so as to coagulate tissue when a second amount of power greater than the first amount of power is delivered to the coagulation electrode during operation of the electrosurgical instrument in a coagulation mode; and
  a user operable switch electrically coupled to the first electrode and to the coagulation electrode for selectively delivering power from a power generator to one or both of the first electrode or the coagulation electrode, the user operable switch providing user selectable switching between the ablation mode and the coagulation mode, wherein
    when operating in the ablation mode, the user operable switch selectively causes the first amount of power to be delivered only to the first electrode and not to the coagulation electrode so as to generate the first current density at the first electrode sufficient to ablate tissue, and
    when operating in the coagulation mode, the user operable switch selectively causes the second amount of power to be delivered to at least the coagulation electrode so as to generate the second current density at the coagulation electrode and optionally also at the first electrode sufficient to coagulate tissue.

26. A method for selectively ablating or coagulating tissue at a surgical site, comprising:
(i) providing an electrosurgical instrument as in claim 25;
(ii) coupling the electrosurgical instrument to an RF generator, the RF generator providing power to the electrosurgical instrument;
(iii) selecting the ablation mode for the electrosurgical instrument using the user operable switch and operating the electrosurgical instrument in the ablation mode, wherein in the ablation mode, the user operable switch causes the first amount of power to be delivered only to the first electrode and not to the coagulation electrode so as to cause ablation of tissue at the surgical site; and
(iv) selecting the coagulation mode for the electrosurgical instrument using the user operable switch and operating the electrosurgical instrument in the coagulation mode, wherein in the coagulation mode, the user operable switch causes the second amount of power to be delivered to the coagulation electrode and optionally also to the first electrode to cause coagulation at the surgical site.

27. An electrosurgical instrument for selectively ablating or coagulating tissue of a patient in a surgical procedure, the electrosurgical instrument being switchable between an ablation mode and a coagulation mode, the electrosurgical instrument comprising:
an elongate probe having a proximal end and a distal end;
a dedicated ablation electrode positioned at a first surface of the distal end of the elongate probe, the dedicated ablation electrode having a first surface area so as to generate a first current density sufficient to ablate tissue when a first amount of power is delivered to the first electrode during operation of the electrosurgical instrument in an ablation mode;
a dedicated coagulation electrode positioned at a second opposing surface of the distal end of the elongate probe and so as to be electrically isolated from the dedicated ablation electrode, the dedicated coagulation electrode having a second surface area greater than the first surface area so as to generate a second current density that is sufficient to coagulate tissue when a second amount of power greater than the first amount of power is delivered to the dedicated coagulation electrode during operation of the electrosurgical instrument in a coagulation mode; and
a user operable switch electrically coupled to the dedicated ablation electrode and to the dedicated coagulation electrode for selectively delivering power from a power generator to one of the dedicated ablation electrode or the dedicated coagulation electrode, the user operable switch providing user selectable switching between the ablation mode and the coagulation mode, wherein
when operating in the ablation mode, the user operable switch selectively causes the first amount of power to be delivered only to the dedicated ablation electrode and not to the dedicated coagulation electrode so as to generate the first current density at the dedicated ablation electrode sufficient to ablate tissue, and
when operating in the coagulation mode, the user operable switch selectively causes the second amount of power to be delivered only to the dedicated coagulation electrode and not to the dedicated ablation electrode so as to generate the second current density at the dedicated coagulation electrode sufficient to coagulate tissue.

28. A method for selectively ablating or coagulating tissue at a surgical site, comprising:
(i) providing an electrosurgical instrument as in claim 27;
(ii) coupling the electrosurgical instrument to an RF generator, the RF generator providing power to the electrosurgical instrument;
(iii) selecting the ablation mode for the electrosurgical instrument using the user operable switch and operating the electrosurgical instrument in the ablation mode, wherein in the ablation mode, the user operable switch causes the first amount of power to be delivered only to the dedicated ablation electrode and not to the dedicated coagulation electrode so as to generate the first current density at the dedicated ablation electrode and cause ablation of tissue at the surgical site; and
(iv) selecting the coagulation mode for the electrosurgical instrument using the user operable switch and operating the electrosurgical instrument in the coagulation mode, wherein in the coagulation mode, the user operable switch causes the second amount of power to be delivered only to the dedicated coagulation electrode and not to the dedicated ablation electrode so as to generate the second current density at the dedicated coagulation electrode and cause coagulation of tissue at the surgical site, and wherein when operating the electrosurgical instrument in the coagulation mode a greater total electrode surface area is activated compared to when operating the electrosurgical instrument in the ablation mode.

29. A method for operating an electrosurgical instrument at a surgical site, comprising:
(i) providing an electrosurgical instrument comprised of multiple electrically isolated electrodes that are independently activatable for selectively varying total active electrode surface area and electrode current density and a user operable switch for allowing a user to select between a coagulation mode and an ablation mode by selectively varying total active electrode surface so as to vary current density;
(ii) coupling the electrosurgical instrument to an RF generator, the RF generator providing power to the electrosurgical instrument;
(iii) selecting the ablation mode using the user operable switch and operating the electrosurgical instrument in the ablation mode, the user operable switch causing power to be delivered to a single electrode that provides a first active electrode surface area with sufficient current density to cause tissue ablation at the surgical site; and
(iv) selecting the coagulation mode using the user operable switch and operating the electrosurgical instrument in the coagulation mode, the user operable switch causing a greater total amount of power to be delivered to multiple electrodes that together provide a second active electrode surface area greater than the first active electrode surface area so as to reduce current density below a threshold required to ablate tissue and so as to cause coagulation of tissue at the surgical site.

30. An electrosurgical instrument for selectively ablating or coagulating tissue of a patient at a surgical site, the electrosurgical instrument being switchable between an ablation mode and a coagulation mode, the electrosurgical instrument comprising: an elongate probe having a proximal end and a distal end; a first electrode positioned on a first surface at the distal end of the elongate probe, the first electrode having a first surface area so as to generate a first current density sufficient to ablate tissue when a first amount of power is delivered to the first electrode during operation of the electrosurgical instrument in an ablation mode; a coagulation electrode positioned at a second opposing surface of the distal end of the elongate probe and so as to be electrically isolated from the first electrode, the coagulation electrode and the first electrode providing a combined surface area greater than the first surface area so as to generate a second current density that is less than the first current density when a second amount of power that is the same or greater than the first amount of power is simultaneously delivered to both the coagulation electrode and the first electrode in order for the coagulation electrode and first electrode to coagulate tissue during operation in a coagulation mode; and a user operable input component or switch electrically coupled to the first electrode and to the coagulation electrode for selectively delivering power from a power generator to only the first electrode during operation of the electrosurgical instrument in the ablation mode and power to both the coagulation electrode and the first electrode during operation of the electrosurgical instrument in the coagulation mode, wherein when the electrosurgical instrument operates in the ablation mode, the user operable input component or switch selectively causes the first amount of power to be delivered only to the first electrode and not to the coagulation electrode so as to generate the first current density at the first electrode sufficient to ablate tissue, and when the electrosurgical instrument operates in the coagulation mode, the user operable input component or switch selectively causes the second amount of power to be simultaneously delivered to both the coagulation electrode and the first electrode so as to generate the second current density at the coagulation electrode and the first electrode that is less than the first current density and that is sufficient to coagulate tissue.

* * * * *

UNITED STATES PATENT AND TRADEMARK OFFICE
CERTIFICATE OF CORRECTION

PATENT NO. : 8,394,088 B2  
APPLICATION NO. : 12/651892  
DATED : March 12, 2013  
INVENTOR(S) : West, Jr.

Page 1 of 1

It is certified that error appears in the above-identified patent and that said Letters Patent is hereby corrected as shown below:

<u>Title Page 2, item (56), Left-hand column</u>
Line 4, change "Sampson et al." to --Truckai et al.--

<u>In the Specification</u>
<u>Column 1</u>
Line 32, change "occurring" to --occurs--

<u>Column 2</u>
Line 66, change "coagulation" to --ablation--

<u>Column 3</u>
Line 47, change "an coagulation" to --a coagulation--

<u>Column 6</u>
Line 24, change "tends" to --tend--

<u>Column 7</u>
Line 13, change "chose" to --choose--

<u>Column 8</u>
Line 62, change "352" to --352b--

<u>Column 10</u>
Line 58, change "lumen" to --lumen 756--

<u>Column 11</u>
Line 47, change "small available" to --small surface area available--

Signed and Sealed this
Twenty-fourth Day of September, 2013

Teresa Stanek Rea
*Deputy Director of the United States Patent and Trademark Office*